(12) United States Patent
Giddis et al.

(10) Patent No.: US 6,891,074 B2
(45) Date of Patent: May 10, 2005

(54) PRODUCTION OF HYDROFLUOROALKANES

(75) Inventors: Clive Robert Giddis, Northwich (GB); Paul Hendry Stewart, Ellesmere Port (GB)

(73) Assignee: Ineos Fluor Holdings Limited (GB)

(*) Notice: Subject to any disclaimer, the term of this patent is extended or adjusted under 35 U.S.C. 154(b) by 0 days.

(21) Appl. No.: 10/362,905

(22) PCT Filed: Sep. 3, 2001

(86) PCT No.: PCT/GB01/03945
§ 371 (c)(1),
(2), (4) Date: May 13, 2003

(87) PCT Pub. No.: WO02/18304
PCT Pub. Date: Mar. 7, 2002

(65) Prior Publication Data
US 2004/0024270 A1 Feb. 5, 2004

(30) Foreign Application Priority Data
Sep. 2, 2000 (GB) .............................. 0021618

(51) Int. Cl.$^7$ ..................... C07C 17/013; C07C 17/04; C07C 17/06; C07C 17/087; C07C 17/07; C07C 17/20; C07C 17/093
(52) U.S. Cl. ..................... 570/167; 570/164; 570/165; 570/166; 570/168
(58) Field of Search ............... 570/164, 165, 570/166, 167, 168

(56) References Cited

U.S. PATENT DOCUMENTS 5,177,275 A    1/1993  Baucom et al.
H1188 H        5/1993  Nappa et al.
6,165,931 A   12/2000  Rao

FOREIGN PATENT DOCUMENTS

| EP | 0 396 168 A1 | 11/1990 |
| EP | 0 449 614 A2 | 10/1991 |
| EP | 0 449 617 A2 | 10/1991 |
| EP | 0 957 074 A1 | 11/1999 |
| GB | 1 307 224 | 2/1973 |
| GB | 1 589 924 | 5/1981 |
| GB | 2 271 989 A | 5/1994 |
| WO | WO 90/08755 A1 | 8/1990 |
| WO | WO 91/06521 A2 | 5/1991 |
| WO | WO 91/13048 A1 | 9/1991 |
| WO | WO 92/00262 A1 | 1/1992 |
| WO | WO 92/16481 A1 | 10/1992 |
| WO | WO 92/19576 A1 | 11/1992 |
| WO | WO 96/13476 A1 | 5/1996 |
| WO | WO 98/21171 A1 | 5/1998 |
| WO | WO 02/018304 A3 | 3/2002 |

OTHER PUBLICATIONS

Henne, et al., "The Addition of Fluorine to Double Bonds," Journal of the American Chemical Society, Jul. 6, 1945, pp. 1639–1640, vol. 67.

Primary Examiner—Elvis O. Price
(74) Attorney, Agent, or Firm—Cook, Alex, McFarron, Manzo, Cummings & Mehler, Ltd.

(57) ABSTRACT

A process for the production of a hydrofluoroalkane, which process comprises contacting a hydrochlorofluoroethane of formula CClXYCFHZ, wherein X and Y are each independently chlorine or fluorine and Z is chlorine, fluorine or hydrogen, in the liquid phase with hydrogen fluoride and a fluorination catalyst and recovering a hydrofluoroalkane from the resulting products.

13 Claims, No Drawings

PRODUCTION OF HYDROFLUOROALKANES

CROSS-REFERENCE TO RELATED APPLICATIONS

This application is a national stage application based upon International Application No. PCT/GB01/03945, filed Sep. 3, 2001, which claims priority from Great Britain Application No. 002168.4, filed Sep. 2, 2000.

The present invention relates to a process for the production of hydrofluoroalkanes, particularly 1,1,1,2-tetrafluoroethane (R-134a) and pentafluoroethane (R-125).

1,1,1,2-tetrafluoroethane (R-134a) is employed as or as a component of a replacement for chlorofluorocarbons in the many applications in which chlorofluorocarbons are employed.

Several processes for the production of hydrofluoroalkanes such as 1,1,1,2-tetrafluoroethane (R-134a) are known. Among such processes is the fluorination of the corresponding chlorine-containing starting materials by reacting the starting material with hydrogen fluoride in the liquid or the vapour phase, usually in the presence of a fluorination catalyst.

GB-A-1589924 describes the production of R-134a by the vapour phase fluorination of 1,1,1-trifluoro-2-chloroethane (R-133a) which is itself obtainable by the fluorination of trichloroethylene as described in GB-A-1307224.

Several processes for the production of R-134a from trichloroethylene based on the combination of the reaction of trichloroethylene with hydrogen fluoride to produce R-133a and the reaction of R-133a with hydrogen fluoride to produce R-134a have been proposed.

WO90/08755 describes the conversion of trichloroethylene to R-134a wherein the two reaction steps are carried out in a single reaction zone wherein part of the product stream containing R-133a is recycled.

EP-A-0449614 describes a process for the manufacture of R-134a which comprises the steps of:

(a) contacting a mixture of trichloroethylene and hydrogen fluoride with a fluorination catalyst under superatmospheric pressure at a temperature of from about 200° C. to about 400° C. in a first reaction zone to form a product containing 1,1,1-trifluoro-2-chloroethane and hydrogen chloride together with unreacted starting materials, (b) passing the product of step (a) together with hydrogen fluoride to a second reaction zone containing a fluorination catalyst at a temperature of from about 280° C. to about 450° C. but higher than the temperature in step (a) to form a product containing 1,1,1-trifluoro-2-chloroethane, 1,1,1,2-tetrafluoroethane and hydrogen chloride, (c) treating the product of step (b) to separate 1,1,1,2-tetrafluoroethane and hydrogen chloride from 1,1,1-trifluoro-2-chloroethane and unreacted hydrogen fluoride, and (d) feeding 1,1,1-trifluoro-2-chloroethane obtained from step (c), together with trichloroethylene and hydrogen fluoride into the first reaction zone (step (a)).

EP-A-0449617 describes a process for the production of R-134a which comprises the steps of:

(a) contacting a mixture of 1,1,1-trifluoro-2-chloroethane and hydrogen fluoride with a fluorination catalyst at a temperature of from about 280° C. to about 450° C. in a first reaction zone to form a product containing 1,1,1,2-tetrafluoroethane and hydrogen chloride together with unreacted starting materials, (b) passing the product of step (a), together trichloroethylene to a second reaction zone containing a fluorination catalyst at a temperature of from about 200° C. to about 400° C. but lower than the temperature in step (a) to form a product containing 1,1,1-trifluoro-2-chloroethane, 1,1,1,2-tetrafluoroethane, hydrogen chloride and unreacted trichloroethylene and hydrogen fluoride, (c) treating the product of step (b) to separate 1,1,1,2-tetrafluoroethane and hydrogen chloride from 1,1,1-trifluoro-2-chloroethane, unreacted trichloroethylene and hydrogen fluoride, and (d) feeding 1,1,1-trifluoro-2-chloroethane obtained in step (c), together with hydrogen fluoride into the first reaction zone (step (a)).

However, a problem which is encountered with processes for the production of 1,1,1,2-tetrafluoroethane based on the hydrofluorination of 1,1,1-trifluoro-2-chloroethane and/or trichloroethylene is that the conversion of 1,1,1-trifluoro-2-chloroethane to 1,1,1,2-tetrafluoroethane is equilibrium limited, there being a relatively low maximum conversion of 1,1,1-trifluoro-2-chloroethane to 1,1,1,2-tetrafluoroethane under typical operating conditions. This process requires repeated recycling of the raw materials. Hence, this process has poor efficiency, as regards energy consumption.

Another commercially used process for the production of 1,1,1,2-tetrafluoroethane involves the following steps:

Each of these reactions goes largely to completion. This process is generally more efficient, as regards energy consumption, than the production of R-134a from trichloroethylene. However, this process has the disadvantage of producing a large amount of hydrogen chloride as a co-product. Additionally, this process requires the use of larger amounts of raw materials.

Other processes for the production of hydrofluoroalkanes such as 1,1,1,2-tetrafluoroethane (R-134a) have been proposed. For example, GB-A-2271989 describes a process in which 1,1,1,2-tetrafluoroethane (R-134a) can be produced by the reaction of $CH_2=CF_2$ and uranium hexafluoride ($UF_6$) at elevated temperature (from about 80° C. to about 400° C.) wherein the molar ratio of $CH_2=CF_2$ to uranium hexafluoride is from 1:1 to 1.2:1.

WO96/13476 describes a vapour phase process for the production of a hydrofluoroalkane that comprises contacting a hydrochlorofluoroethane or hydrochlorofluoroethene with hydrogen fluoride and a fluorination catalyst such as a chromia catalyst.

WO92/00262 describes a process in which unfluorinated haloolefins, such as trichloroethylene (CHCl=CCl$_2$) are converted to fluorinated saturated products such as 1,1,1,2-tetrafluoroethane (R-134a) using a molten alkali metal acid fluoride. Yields of 1,1,1,2-tetrafluoroethane (R-134a) are, however, generally quite low using this method.

Various processes for producing hydrofluoroalkanes such as 1,1,1,2-tetrafluoroethane (R-134a) by replacing the chlorine atom of the —CH$_2$Cl group of CF$_3$CH$_2$Cl (R-133a) with F have been attempted and reported, see, for example, the prior art discussion in WO91/13048. It is, however, well known that the chlorine atom of the —CH$_2$Cl group of, for example CF$_3$CH$_2$Cl (R-133a), is highly resistant to fluorination, particularly by halogen exchange with HF. A process in which $CF_3CH_2Cl$ (R-133a) is reacted with MF, wherein M is at least one alkali metal having an atomic number of from 19 to 55, to produce 1,1,1,2-tetrafluoroethane (R-134a) is described in WO91/13048. In that process a solid composition consisting essentially of the alkali metal fluoride is contacted with gaseous $CF_3CH_2Cl$ (R-133a) at a temperature at which both $CF_3CH_2Cl$ (R-133a) and 1,1,1,2-tetrafluoroethane (R-134a) are in a gaseous state.

It is an object of the present invention to provide a process for the production of hydrofluoroalkanes such as 1,1,1,2-tetrafluoroethane (R-134a) which avoids a number of the problems associated with the processes of the prior art.

By the term "hydrofluoroalkane(s)" is meant alkanes which contain carbon, hydrogen and fluorine only.

In particular, the present invention avoids the problems associated with the conversion of $CF_3CH_2Cl$ (R-133a) to 1,1,1,2-tetrafluoroethane (R-134a) by providing a route for the production of 1,1,1,2-tetrafluoroethane (R-134a) which does not require the use of $CF_3CH_2Cl$ (R-133a).

The present invention also seeks to provide a more energy efficient process for the production of hydrofluoroalkanes, this is achieved by providing a liquid phase process.

Other problems, which the present invention seeks to address, include reduction of co-product production, especially HCl production and improved percentage conversion of the starting materials to the product.

The present invention, therefore, provides a process for the production of a hydrofluoroalkane, particularly 1,1,1,2-tetrafluoroethane or pentafluoroethane, which process comprises contacting a hydrochlorofluoroethane with hydrogen fluoride and a fluorination catalyst and recovering a hydrofluoroalkane from the resulting products.

The hydrochlorofluoroethane typically has the formula CClXYCFHZ wherein X and Y are each independently chlorine or fluorine and Z is chlorine, fluorine or hydrogen, preferably chlorine or hydrogen. For example, the hydrochlorofluoroethane may have the formula $CClXYCFH_2$.

In a particular embodiment of the invention, the process of the invention is a process for the production of 1,1,1,2-tetrafluorethane and the hydrochlorofluoroethane has the formula $CClXYCFH_2$, for example $CCl_2FCFH_2$.

In a particular embodiment of the invention, the process of the invention is a process for the production of pentafluoroethane and the hydrochlorofluoroethane is, for example, $CCl_2FCClFH$.

More specifically, the present invention provides a process for producing 1,1,1,2-tetrafluoroethane (R-134a) from 1,1-dichloro-1,2-difluoroethane $CH_2FCCl_2F$ (R-132c) by the hydrofluorination of $CH_2FCCl_2F$ (R-132c) with hydrogen fluoride.

It has been found that the reaction products from the process of the invention for producing 1,1,1,2-tetrafluoroethane comprise a greater molar proportion of 1,1,1,2-tetrafluorethane than is obtained when 1,1,1-trifluoro-2-chloroethane is used as the starting material.

The starting materials are $CCl_3CFH_2$, $CCl_3CF_2H$, $CCl_2FCFH_2$, $CCl_2FCF_2H$, $CClF_2CFH_2$, $CClF_2CF_2H$, $CCl_2FCClFH$, $CCl_3CClFH$ and $CClF_2CClFH$. Preferably $CCl_2FCFH_2$ or $CClF_2CFH_2$ is employed for the production of 1,1,1,2-tetrafluoroethane. Preferably $CCl_2FCClFH$ or $CCl_2FCF_2H$ is employed for the production of pentafluoroethane.

Typically, when $CCl_2FCFH_2$ (R-132c) is employed $CClF_2CFH_2$ (R-133b) is produced as an intermediate. This intermediate is further fluorinated to produce $CF_3CFH_2$ (R-134a). The conversion of $CCl_2FCFH_2$ (R-132c) to $CF_3CFH_2$ (R-134a) via $CClF_2CFH_2$ typically takes place in a single reaction vessel. However, it is possible for $CCl_2FCFH_2$ (R-132c) to be partly fluorinated to produce $CClF_2CFH_2$ (R-133b) which is isolated and subsequently fluorinated to produce $CF_3CFH_2$ (R-134a).

The process of the invention typically takes place at a relatively low temperature, for example below 150° C. in the liquid phase in the presence of a catalyst. The process can be carried out in batch, semi-batch or continuous modes.

Reaction times are dependent on several factors such as the catalyst used, the HF concentration, the pressure and the reaction temperature. For batch processes, suitable reaction times are from 1 to 24 hours. For example 15 to 18 hours, such as 16 or 17 hours.

Any suitable fluorination catalyst can be used. Examples of the fluorination catalyst include, but are not limited to, halides, mixed halides or oxyhalides of groups 4, 5, 6, 8, 9, 10, 13, 15 and 16 of the Periodic Table. Suitable fluorination catalysts are those which yield the desired hydrofluoroalkane as a product of the reaction with a yield of greater than 10%, preferably greater than 25%, based on the starting materials processed.

Suitable catalysts include antimony pentahalides, such as those represented by the formula $SbCl_{5-x}F_x$, wherein x is greater than 0 and less than or equal to 5. Antimony pentahalides in which x is greater than 0 and less than or equal to 4 or less than or equal to 3 may be used. For example, x may be from 1 to 3 (eg 2). The use of antimony halides wherein x is 3 is preferred. x is not necessarily a whole number. Suitable antimony pentahalides include, for example, $SbF_5$, $SbF_4Cl$, $SbFCl_4$, $SbCl_3F_2$ and $SbCl_2F_3$. A mixture of two or more halide catalysts may be used, for example a mixture of $SbCl_3F_2$ and $SbCl_4F$ may be used. If, for example, a 1:1 molar mixture of $SbCl_3F_2$ and $SbCl_4F$ were used the catalyst could be represented as $SbCl_{3.5}F_{1.5}$. It is, of course, not essential that the different halide compounds are present in a ratio of 1:1. The ratio of any two halide compounds within a catalyst mixture may, typically, be from 1:1000 to 1000:1.

Another antimony catalyst that may be used is $HSbF_6$.

Other suitable catalysts include halides, mixed halides or oxyhalides of tin, tungsten, titanium, tantalum, molybdenum and niobium.

Suitable tin containing catalysts include those of formula $SnCl_{4-x}F_x$, wherein x is greater than 0 and less than or equal to 4. x may, for example, be 1, 2, 3 or 4. x is not necessarily a whole number. Examples of suitable tin containing catalysts include tin tetrafluoride ($SnF_4$) and mixed halides such as $SnCl_3F$, $SnCl_2F_2$ and $SnClF_3$.

Suitable tungsten containing catalysts include those of formula $(WCl_{5-x}F_x)_2$, wherein x is greater than 0 and less than or equal to 5. Tungsten halides in which z is greater than 0 and less than or equal to 4 or less than or equal to 3 may be used. For example x may be from 1 to 3 (eg 2). x is not necessarily a whole number. Examples of suitable tungsten containing catalysts include tungsten pentafluoride $((WF_5)_2)$, $(WF_4Cl)_2$, $(WFCl_4)_2$, $(WCl_3F_2)_2$ and $(WCl_2F_3)_2$.

Suitable titanium containing catalysts include those of formula $TiCl_{4-x}F_x$, wherein x is greater than 0 and less than or equal to 4. x may for example, be 1, 2, 3 or 4. x is not necessarily a whole number. Examples of suitable titanium containing catalysts include titanium tetrafluoride ($TiF_4$) and mixed halides such as $TiCl_3F$, $TiCl_2F_2$ and $TiClF_3$.

Suitable tantalum containing catalysts include those of formula $TaCl_{5-x}F_x$, wherein x is greater than 0 and less than or equal to 5. Tantalum halides in which x is greater than 0 and less than or equal to 4 or less than or equal to 3 may be used. For example x may be from 1 to 3 (eg 2). x is not necessarily a whole number. Examples of suitable tantalum containing catalysts include tantalum pentafluoride ($TaF_5$), $TaF_4Cl$, $TaFCl_4$, $TaCl_3F_2$ and $TaCl_2F_3$. The use of tantalum pentafluoride is particularly preferred.

Suitable molybdenum containing catalysts include those of formula $MoCl_{5-x}F_x$, wherein x is greater than 0 and less than or equal to 5. Molybdenum halides in which x is greater than 0 and less than or equal to 4 or less than or equal to 3 may be used. For example, x may be from 1 to 3 (eg 2). x is not necessarily a whole number. Examples of suitable molybdenum containing catalysts include molybdenum pentafluoride ($MoF_5$), $MoF_4Cl$, $MoFCl_4$, $MoCl_3F_2$ and $MoCl_2F_3$.

Suitable niobium containing catalysts include those of formula $NbCl_{5-x}F_x$, wherein x is greater than 0 and less than or equal to 5. Niobium halides in which x is greater than 0 and less than or equal to 4 or less than or equal to 3 may be used. For example, x may be from 1 to 3 (eg 2). x is not necessarily a whole number. Examples of suitable niobium containing catalysts include niobium pentafluoride ($NbF_5$), $NbF_4Cl$, $NbFCl_4$, $NbCl_3F_2$ and $NbCl_2F_3$.

Mixtures of any of the catalysts mentioned above may be used. For example, a combination of an antimony catalyst and a tin catalyst or an antimony catalyst and a titanium catalyst may be used. Each of the catalysts mentioned above can be used alone or in combination with any one or more of the other catalysts mentioned.

The catalysts used in the present invention are typically prepared by charging the reactor with the metal halide(s) (for example, $SbCl_5$, $SnCl_4$, $(WCl_5)_2$, $TiCl_4$, $TaCl_5$, $MoCl_5$ or $NbCl_5$ or a mixture thereof) and pretreating the metal halide(s) with HF to achieve at least partial fluorination. The metal chloride may itself be made in-situ in the reaction vessel.

Alternatively, partially or fully fluorinated catalysts, or mixtures thereof, may be charged directly to the reactor and subsequently pre-treated with HF.

Alternatively, metal oxides or mixtures of metal oxides may be charged directly to the reactor and subsequently pre-treated with hydrogen fluoride. Suitable metal oxides include $Ta_2O_5$, $Nb_2O_5$, $W_2O_5$, $Mb_2O_5$, $Sb_2O_5$, $TiO_2$ and $SnO_2$. Preferred metal oxides are $Ta_2O_5$ and $Nb_2O_5$.

Preferably a tantalum catalyst or an antimony catalyst is used. Optionally, when an antimony catalyst is used, chlorine may be added to the reaction vessel to ensure that the antimony is maintained in the $^+5$ oxidation state.

The selection of the catalyst to be used will depend on a number of factors, including the reaction conditions and the rate of production of the fluorinated product. While we do not wish to be bound by theory, it seems that the amount of fluorination of the pentahalide catalyst alters with the rate of production of the fluorinated product. For higher rates of production of the fluorinated product a more fluorinated catalyst is required.

The weight ratio of organic starting material to catalyst is typically from 1:50 to 5:1, preferably from 1:10 to 1:1.

The relative proportions of hydrogen fluoride to starting material that is employed may vary within wide limits although it is generally preferred to employ at least a stoichiometric amount of hydrogen fluoride. The stoichiometrically required molar ratio depends upon the particular starting material. It is generally advantageous to use excess hydrogen fluoride, typically 1 to 50 times the stoichiometric amount and preferably 1 to 20 times the stoichiometric amount. However, for some metals, such as antimony, this can lead to the formation of highly corrosive acid complexes. Therefore, for metals like antimony, which can form high corrosive acid complexes, hydrogen fluoride is typically only added in an amount in excess of the stoichiometrically required amount if additional hydrogen fluoride is required to replace lost hydrogen fluoride, for example if hydrogen fluoride is removed from the reaction vessel with the reaction products.

Alternatively, an excess of organic starting material may be used. In this case, the rate of reaction is controlled by the rate of addition of hydrogen fluoride.

The contents of the reaction vessel may be mixed using any technique that is standard in the art. For example, an agitator may be used to mix the contents. Alternatively, the momentum of the reactants (for example the hydrogen fluoride) as they are added to the reaction vessel may be sufficient to allow adequate mixing. Alternatively, at least one of the reactants may be added as a vapour or as a mixture of vapour and liquid, to promote mixing.

The fluorinated product of the process of the invention is typically more volatile than the organic starting material. The fluorinated product can, for example be removed from the reaction vessel as a vapor. The by-product, hydrogen chloride, can also be removed from the reaction vessel as a vapor. Other light impurities will typically be removed from the reaction vessel along with the fluorinated product and the hydrogen chloride. Optionally, heavy impurities can be periodically or continuously removed from the reaction vessel. For example, a mixture of catalyst and heavy impurities can be purged periodically or continuously from the reactor. It is possible to separate the catalyst from the heavy impurities and then retain the catalyst for later use or return it to the reactor.

The temperature at which the process of the invention is carried out is typically less than 150° C. Preferably the temperature is from 50 to 120° C., most preferably 70 to 100° C. Suitable temperatures include, for example, those from 90° C. to 100° C. As will be readily appreciated, the most suitable temperature will depend on a number of factors such as the pressure at which the reaction is carried out and the nature of the catalyst and starting materials used.

The process is typically carried out at a pressure of from 0 to $60 \times 10^5$ $N/m^2$ (0 to 60 bar), preferably from $6 \times 10^5$ to $50 \times 10^5$ $N/m^2$ (6 to 50 bar). Especially preferred pressures are those in the range of $40 \times 10^5$ to $45 \times 10^5$ $N/m^2$ (40 to 45 bar), for example $44 \times 10^5$ $N/m^2$ (44 bar). Other examples of suitable pressures include $20 \times 10^5$ to $30 \times 10^5$ $N/m^2$ (20 to 30 bar). The pressure will be at least equal to the vapour pressure of the reaction mixture. As will be readily appreciated, the most suitable pressure will depend on a number of factors such as the temperature at which the reaction is carried out and the nature of the catalyst and starting materials used.

Suitable combinations of temperature and pressure include 40 bar at 90° C. and 44 bar at 100° C.

The hydrogen fluoride used in the present invention is typically substantially anhydrous. As used herein, the term "substantially anhydrous" refers to a moisture content of less than about 0.05% by weight and preferably less than about 0.02% by weight. The presence of water tends to deactivate the fluorination catalyst. Water tends to oxidize the metal halides to inactive oxides. The presence of water can be compensated for to some extent by increasing the amount of catalyst used or by the addition of chlorine to the reactor.

The products of the process of the present invention may be separated and/or purified using standard techniques well known in the art such as distillation. The products may be washed with water to remove any excess hydrogen fluoride.

Optionally, any underfluorinated products can be recycled into the reaction vessel where they can undergo further fluorination. For example, any CClF$_2$CFH$_2$ produced in a reaction process for the production of CF$_3$CFH$_2$ (R-134a) can be recycled into the reaction vessel where it can undergo further fluorination to provide of CF$_3$CFH$_2$ (R-134a).

The starting materials used in the present invention can be produced by any suitable method known in the art. Commercially available starting materials may be used.

For example, GB-A-2271989 describes a process for the preparation of fluorinated ethanic organic compounds, which comprises reacting ethylene or a halogenated ethylenic compound with uranium hexafluoride. 1,1-dichloro-1,2-difluoroethane (R-132c) may be produced using the process described in GB-A-2271989. In that process, vinylidene dichloride, CH$_2$=CCl$_2$, is reacted with uranium hexafluoride at high temperature, the molar ratio of vinylidene dichloride to uranium hexafluoride typically ranges from 1:1 to 1.2:1. The production of CCl$_2$FCClFH is also described in GB-A-2271989. The production of CHClFCCl$_2$F (R-122a) using uranium hexafluoride is also described in "Production of Ozone-safe Substances by Fluorination of Organic Compounds with the Use of Depleted Uranium Hexafluoride", in The Proceedings of the 16$^{th}$ International Symposium on Fluorine Chemistry (2000), published by the Royal Society of Chemistry.

1,1-Dichloro-1,2-difluoroethane (R-132c) can be synthesized by oxyfluorination of 1,1-dichloroethene (vinylidene dichloride) using lead (IV) oxide in anhydrous hydrogen fluoride as described in J. Am. Chem. Soc., 1945, 67, 1639. The reaction can be carried out in a Hastalloy C autoclave. This reaction yields a considerable amount of a co-product, 1,1-dichloro-1-fluoroethane (R-141b). The resulting reaction mixture is fractionally distilled and a fraction comprising 60% R-141b and 40% R-132c by weight is collected. It is not, however, feasible to separate R-132c and R-141b by distillation.

The preparation of 1,1-dichloro-1,2-difluoroethane is also described in Example 4 of WO92/00262. Other processes which can be used to produce 1,1-dichloro-1,2-difluoroethane, 1,1,1-trichloro-fluoroethane and 1-chloro-1,1,2-trifluoroethane include that described in WO91/13048.

1,1-dichloro-1,2-difluoroethane can also be produced by a process comprising contacting 1,1-dichloroethylene with lead dioxide and anhydrous hydrogen fluoride as described in United States Statutory Invention Registration number H1188.

Preferably 1,1-dichloro-1,2-difluoroethane CH$_2$FCCl$_2$F (R-132c) is prepared using the process described in EP-A-396168 (which corresponds to U.S. Pat. No. 5,177,275), which is incorporated herein by reference. That process comprises the steps of:

(a) reacting
(i) a substrate compound having at least one site for fluorination, such as vinylidene dichloride, CH$_2$=CCl$_2$, or a mixture of such compounds with
(ii) elemental fluorine, alone, or in admixture with an inert gas, in an eductor until the reaction is substantially complete; and (b) recovering (i) a reacted substrate compound, (ii) a mixture of such compounds or (iii) an oligomeric derivative of (i) or (ii).

Preferably the process is carried out in a loop reactor comprising cooling zones for controlling the heat of reaction with fluorine. Preferably, the reaction temperature is from about −80° C. to about +100° C. The process can be carried out with a reaction mixture consisting essentially of (a)(i) and (a)(ii); alternatively, the process can be carried out with a reaction mixture comprising (a)(i), (a)(ii) and (a)(iii), in a liquid medium at a temperature of from about the freezing point of the medium to about the boiling point of the medium. For example, the process can be carried out with a reaction mixture of vinylidene dichloride and fluorine, optionally in a liquid medium, at a temperature of from about the freezing point of the liquid medium to about the boiling point of the liquid medium. If a liquid medium is used, it preferably comprises a perhalogenated organic liquid or an inorganic liquid selected from water, hydrogen fluoride, and the like or a mixture thereof. Suitable liquid mediums include CFCl$_3$, CF$_2$Cl$_2$, and CCl$_4$.

Any other suitable process for the production of 1,1-dichloro-1,2-difluoroethane CH$_2$FCCl$_2$F (R-132c) from vinylidene dichloride (CH$_2$=CCl$_2$) may alternatively be used.

If necessary, CH$_2$FCCl$_2$F (R-132c) can be purified by any process known in the art, such as the one described in WO91/06521. It is preferable for CH$_2$FCCl$_2$F (R-132c) to be purified before it is used for the production of 1,1,1,2-tetrafluoroethane (R-134a).

In a preferred embodiment, the present invention provides a two step process for the production of 1,1,1,2-tetrafluoroethane (R-134a). In the first step, vinylidene dichloride (VdC, CH$_2$CCl$_2$) is reacted with fluorine to form R-132c (CH$_2$FCCl$_2$F) and subsequently R-132c is fluorinated to form R-134a. These steps are represented by the following equations:

The two steps of this process can be carried out adjacently and continuously. For example, with the reaction products of the first stage being fed directly into the reaction vessel for the second stage. Alternatively, the two stages can be performed separately. For example, R-132c (CH$_2$FCCl$_2$F) can be prepared and stored until it is required for the production of 1,1,1,2-tetrafluoroethane (R-134a). In other words, it is not necessary for R-132c to be produced at the location at which it is converted to 1,1,1,2-tetrafluoroethane (R-134a). Commercially available R-132c may be used to produce 1,1,1,2-tetrafluoroethane (R-134a) in accordance with the present invention. It is also possible that both the conversion of vinylidene dichloride to R-132c and the conversion of R-132c to 1,1,1,2-tetrafluoroethane (R-134a) could be performed in a single reactor.

The present invention is illustrated by the following non-limiting Example.

EXAMPLE

Preparation of 1,1,1,2-tetrafluoroethane (R-134a) from 1,1-dichloro-1,2-difluoroethane (R-132c) Using a Tantalum Pentafluoride Catalyst in the Liquid Phase A 25 ml Hastelloy C pressure reactor, fitted with a pressure gauge, stirrer, thermocouple pocket, dip pipe and vent line was charged with 5 grams of tantalum pentafluoride in a dry box. The vessel was assembled and pressure tested to 25 barg with nitrogen.

The vessel was then depressurised to atmospheric pressure and charged with 12 grams of hydrogen fluoride. The stirrer was then switched on. A 5 gram aliquot of R-132c was added to the reaction vessel and the heater was switched on.

The vessel was heated to 100° C. and held at this temperature for one hour. The pressure generated at 100° C. was 44 barg. The reactor was cooled to 90° C. and held at this temperature for a further 16 hours. The pressure at 90° C. was 40 barg.

The reactor was cooled to 0° C. (pressure of 18 barg) and the contents of the headspace transferred into a cooled Whitey bomb. A total of 4 grams of material were recovered.

20 mls of the recovered vapour was added to a 300 ml glass burette containing 5 mls of water. Analysis of the organic fraction present in the burette was carried out using conventional gas chromatographic techniques. The composition of the headspace (based on area counts) was as follows:

| | |
|---|---|
| 1,1,1,2-tetrafluoromethane (R-134a): | 81–83% |
| Others (mainly R-133b and its isomers plus R-132c): | 17–19% |

What is claimed is:

1. A process for the production of a hydrofluoroalkane, which process comprises contacting a hydrochlorofluoroethane of formula CClXYCFHZ, wherein X and Y are each independently chlorine or fluorine and Z is chlorine, fluorine or hydrogen, in the liquid phase with hydrogen fluoride and a fluorination catalyst and recovering a hydrofluoroalkane from the resulting products.

2. A process according to claim 1, wherein the catalyst is selected from $SbCl_{5-x}F_x$, $(WCl_{5-x}F_x)_2$, $TaCl_{5-x}F_x$, $MoCl_{5-x}F_x$ and $NbCl_{5-x}F_x$ wherein x is greater than 0 and less than or equal to 5, $TiCl_{4-x}F_x$ and $SnCl_{4-x}F_x$, wherein x is greater than 0 and less than or equal to 4 and mixtures thereof.

3. A process according to claim 2, wherein the catalyst comprises at least one compound of the formula $TaCl_{5-x}F_x$ wherein x is greater than 0 and less than or equal to 5.

4. A process according to claim 3, wherein the catalyst is tantalum pentafluoride.

5. A process according to claim 3, wherein the catalyst comprises at least one compound of the formula $TaCl_{5-x}F_x$ wherein x is greater than 0 and less than or equal to 4.

6. A process according to claim 2, wherein the catalyst comprises at least one compound of the formula $SbCl_{5-x}F_x$ wherein x is greater than 0 and less than or equal to 5.

7. A process according to claim 1, wherein the hydrofluoroalkane is 1,1,1,2-tetrafluoroethane.

8. A process according to claim 1, wherein the hydrochlorofluoroethane is 1,1-dichloro-1,2-difluoroethane or 1-chloro-1,1,2-trifluoroethane.

9. A process according to claim 8, wherein the 1,1-dichloro-1,2-difluoroethane has been obtained by the reaction of vinylidene dichloride with elemental fluorine.

10. A process according to claim 1, wherein the hydrofluoroalkane is pentafluoroethane.

11. A process according to claim 10, wherein the hydrochlorofluoroethane is 1,1,2-trichloro-1,2-difluoroethane or 1,1-dichloro-1,2,2-trifluoroethane.

12. A process according to claim 1, which is carried out batch-wise.

13. A process according to claim 1 which is carried out continuously.

* * * * *